(12) United States Patent
Young et al.

(10) Patent No.: US 12,678,325 B2
(45) Date of Patent: Jul. 14, 2026

(54) HUMAN EXTREMITY WARMING APPARATUS

(71) Applicant: TDMD, LLC, Pocatello, ID (US)

(72) Inventors: Rustyn Young, Pocatello, ID (US);
Candi Young, Pocatello, ID (US)

( * ) Notice: Subject to any disclaimer, the term of this patent is extended or adjusted under 35 U.S.C. 154(b) by 618 days.

(21) Appl. No.: 18/082,313

(22) Filed: Dec. 15, 2022

(65) Prior Publication Data

US 2023/0233368 A1     Jul. 27, 2023

Related U.S. Application Data

(60) Provisional application No. 63/303,619, filed on Jan. 27, 2022.

(51) Int. Cl.
*A61F 7/02*          (2006.01)

(52) U.S. Cl.
CPC .......... *A61F 7/02* (2013.01); *A61F 2007/023* (2013.01); *A61F 2007/0246* (2013.01); *A61F 2007/0249* (2013.01)

(58) Field of Classification Search
CPC ........ A61F 2007/0045; A61F 2007/023; A61F 2007/0231; A61F 2007/0246; A61F 2007/0249; A61F 7/007; A61F 7/02; A61F 7/08
See application file for complete search history.

(56) References Cited

U.S. PATENT DOCUMENTS

| | | | | |
|---|---|---|---|---|
| 4,676,247 A | * | 6/1987 | Van Cleve ................ | A61F 7/02 |
| | | | | 62/530 |
| 4,981,135 A | * | 1/1991 | Hardy ....................... | A61F 7/02 |
| | | | | 607/108 |
| 6,656,210 B1 | * | 12/2003 | Plewes ...................... | A61F 7/02 |
| | | | | 607/114 |
| D671,225 S | | 11/2012 | Higley | |
| 2010/0152823 A1 | * | 6/2010 | Muchowicz ............. | A61F 7/10 |
| | | | | 607/108 |
| 2017/0095368 A1 | * | 4/2017 | Hess ......................... | A61F 7/02 |

* cited by examiner

*Primary Examiner* — Tigist S Demie

(57)          ABSTRACT

A human extremity warming apparatus includes a first strap and a second strap with a housing positioned thereinbetween. The warming apparatus includes a warming device. The warming device has an upper surface and a lower surface. The upper surface may have a first sheet of material. The first sheet of material may include a heat-transferring material that provides heat to a user at a first temperature. The lower surface may have a second sheet of material that includes a protective layer that transfers heat to the skin at a second temperature. The upper surface and lower surface may be color coded or have other indicia to assist a user in determining the type of heating surface. The apparatus may be adjusted to fit on the wrists or legs of a user.

10 Claims, 15 Drawing Sheets

HUMAN EXTREMITY WARMING APPARATUS

CROSS-REFERENCE TO RELATED APPLICATIONS

This application claims the benefit of U.S. Provisional Application Ser. No. 63/303,619, filed on Jan. 27, 2022, which is incorporated herein by reference.

TECHNICAL FIELD

The present disclosure relates to a human extremity warming apparatus. More particularly, the present disclosure relates to an apparatus that is coupleable to, for example, a wrist, thigh, and/or an ankle to provide warmth to a human extremity.

BACKGROUND

Cold weather often arrives during the winter, and other seasons, in many places throughout the country. With cold weather, many experience uncomfortable physical conditions, which physiologically change the human body. When the human body is introduced into a cold climate, it will attempt to retain heat around the vital organs, like the heart and lungs. This occurs by vasoconstriction, the constricting of the arteries (e.g., ulnar and radial arteries) and other vessels in the extremities, which prevents loss of heat from the skin surface and moves heat towards the vital organs. Accordingly, cold extremities come from physiological changes due to the human body becoming cool. Because of these changes, extremities, such as hands and feet, may be damaged and have numbness and/or frost bite if exposed to the elements for too long.

To combat these cold conditions and their effects on extremities, some may stay inside and limit outside exposure, others may utilize gloves, and others may utilize hand warmers or a combination of all three. There are many different types of gloves both in material and type to address the varying climates throughout the world. Handwarmers may be placed within a pair of gloves or within pockets. There are a variety of different handwarmers on the market, such as HotHands® and Zippo®, with some differences in functionality. For instance, handwarmers may function by a chemical reaction, battery, or lighter fluid.

Gloves and handwarmers are important and solve many issues; however, they also have many shortcomings. For example, gloves may differ in quality and material. As such, some gloves may be inadequate to prevent cold weather from damaging hands. Furthermore, utilizing handwarmers with gloves may address only some of the issues of inadequate gloves or keeping hands warm. Handwarmers are loose in the hand, which makes it difficult to use hands while also holding handwarmers. However, even with this combination of a handwarmer in hand and a glove, vasoconstriction can still occur, leading to cold or damaged extremities.

Accordingly, there is a need for an apparatus to curtail the effects of vasoconstriction in the extremities so as to maintain blood flow and ultimately, warmth in cold climates. The present invention seeks to solve these and other problems.

SUMMARY OF EXAMPLE EMBODIMENTS

In one embodiment, a human extremity warming apparatus (hereinafter referred to as the "warming apparatus") comprises a first strap and a second strap with a compartment interposed thereinbetween. The compartment may comprise an upper surface, a lower surface, a first side, and a second side. The first strap may comprise a first end and a second end. The first end may be coupleable to the compartment, and the second end may comprise a first fastener. The second strap may comprise a third end and a fourth end. The third end may be coupleable to the compartment on a side opposite the first end, and the fourth end may comprise a second fastener.

The warming apparatus comprises a warming device. The warming device comprises an upper surface and a lower surface. The upper surface may comprise a first sheet of material. The first sheet of material may comprise a heat transferring material that provides the most heat to a user. The upper surface may be coupled to the compartment via upper surface fasteners. The lower surface may comprise a second sheet of material that comprises a protective layer that transfers heat to the skin but prevents any burns upon the skin. The lower surface may be coupled to the compartment via lower surface fasteners. In some embodiments, the upper surface and lower surface may be color coded or have other indicia to assist a user in determining the type of heating surface.

In one embodiment, a warming apparatus comprises a first strap and a second strap with a housing interposed thereinbetween. The housing may comprise an upper surface and a lower surface. The first strap may comprise a first end. Approximate the first end the first strap may comprise a loop. The second strap may comprise a second end that can be inserted into the loop so as to couple the second strap to the first strap. The upper surface of the housing may comprise a first opening and a second opening capable of receiving a warming device. The upper surface may have upper surface vents to allow the heat to escape from the warming device and contact the body of a user. The lower surface of the housing may comprise a third opening and a fourth opening capable of receiving a warming device. The lower surface may have lower surface vents. The lower surface vents may be less in number than the upper surface vents.

In one embodiment, a warming apparatus comprises a first strap and a second strap with a housing interposed thereinbetween. The first strap, second strap, and housing may be a single unit. In some embodiments, the warming apparatus may be disposable. The housing may comprise a warming device. The first strap may couple to the second strap via a first fastener and a second fastener.

In one embodiment, a warming apparatus comprises a first strap with a housing. The warming apparatus may be configured to wrap around the legs of livestock. The first strap may couple to the housing via a first fastener on the first strap and a second fastener on the housing. The first fastener and second fastener may include hook and loop so as to be adjustable. In some embodiments, the first fastener may extend past an end of the first strap, thereby allowing the warming apparatus to fit numerous sizes of livestock legs.

In one embodiment, a warming apparatus comprises a first strap and a second strap with a housing interposed thereinbetween. The housing may comprise a housing fastener that may be opened and closed so as to secure a warming device therein. The housing may include a window. The window may be covered by a screen that is manufactured out of a first material. The first material may include a mesh material or other heat-permeable material. The user may couple the first strap to the second strap via a first fastener on the second strap.

In one embodiment, a warming apparatus may be positioned in a sleeve, cuff, of an article of clothing so as to be placed against a user's lower wrist. The warming apparatus may comprise a housing and a fastener to provide access to the housing.

In one embodiment, a warming apparatus comprises a first strap and a second strap with a housing interposed thereinbetween. The warming apparatus may comprise a first layer of material and a second layer of material. The housing may be created between the first layer and the second layer. The housing may be separate from the first and second straps. The housing, when separated, may create an opening to receive the warming device. The housing may comprise a first housing fastener positioned on the first layer in the opening and a second housing fastener positioned on the second layer in the opening. The first strap may comprise a first fastener and the second strap may comprise a second fastener. The first fastener may couple to the second fastener and be adjusted to fit any user.

BRIEF DESCRIPTION OF THE DRAWINGS

FIG. 9A illustrates a top plan view of a human extremity warming apparatus;

DETAILED DESCRIPTION OF EXAMPLE EMBODIMENTS

Figure 1:
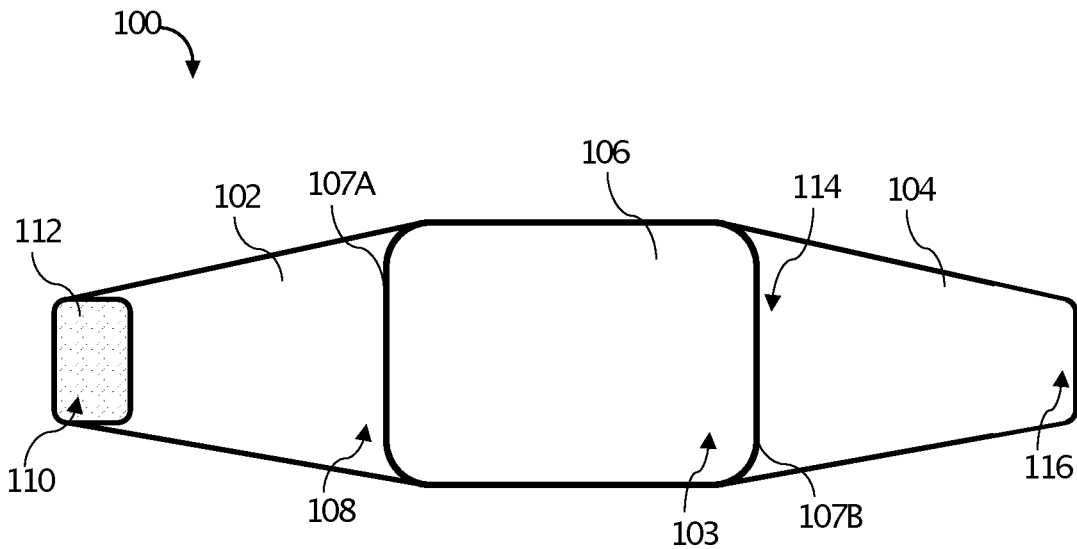
FIG. 1 illustrates a top plan view of a human extremity warming apparatus.

While embodiments of the present disclosure may be subject to various modifications and alternative forms, specific embodiments have been shown by way of example in the drawings and will be described in detail herein. However, the present disclosure is not intended to be limited to the particular features, forms, components, etc. disclosed. Rather, the present disclosure will cover all modifications, equivalents, and alternatives falling within the scope of the present disclosure.

Reference to the invention, the present disclosure, or the like are not intended to restrict or limit the invention, the present disclosure, or the like to exact features or steps of any one or more of the exemplary embodiments disclosed herein. References to "one embodiment," "an embodiment," "alternate embodiments," "some embodiments," and the like, may indicate that the embodiment(s) so described may include a particular feature, structure, or characteristic, but not every embodiment necessarily includes the particular feature, structure, or characteristic.

Any arrangements herein are meant to be illustrative and do not limit the invention's scope. Although specific terms are employed herein, they are used in a generic and descriptive sense only and not for purposes of limitation. Unless otherwise defined herein, such terms are intended to be given their ordinary meaning not inconsistent with that applicable in the relevant industry and without restriction to any specific embodiment hereinafter described.

It will be understood that the steps of any such processes or methods are not limited to being carried out in any particular sequence, arrangement, or with any particular graphics or interface. In fact, the steps of the disclosed processes or methods generally may be carried out in various, different sequences and arrangements while still being in the scope of the present invention. Certain terms are used herein, such as "comprising" and "including," and similar terms are meant to be "open" and not "closed" terms. These terms should be understood as, for example, "including, but not limited to."

As previously described, there is a need for an apparatus to curtail the effects of vasoconstriction in the extremities so as to maintain blood flow and ultimately, warmth in cold climates. The present invention seeks to solve these and other problems.

Cold weather brings uncomfortable conditions for many throughout the world. Some may live and/or work in these conditions. When the human body experiences cold weather, it changes physiologically. As an example, once the human body begins to cool down, the body attempts to prevent too much heat from leaving the surface of the skin. Accordingly, capillaries, veins, and arteries will begin to constrict so as to move blood supplies to the vital organs. To combat this physiological change, many turn to gloves, mittens, warming devices, etc. to keep hands, legs, and feet warm. By using these items, an individual can attempt to reduce the likelihood of vasoconstriction and thus, cold extremities. However, even with the use of items, such as gloves and hand warmers in the gloves, they may still be inadequate to address the issue of vasoconstriction. If that is the case, extremities will remain cold and the individual may not only be uncomfortable but receive damage to his/her tissue.

A human extremity warming apparatus described herein seeks to prevent vasoconstriction in the hands and/or the feet by warming the arteries that supply those extremities. The extremity warming apparatus may comprise a strap that is coupleable to a wrist or ankle of a user. The strap may have a compartment, or, in some embodiments, a housing, thereon to receive a warming device. The compartment with the warming device is positioned so as to rest upon the arteries and veins found within the wrist, ankle, or other parts of the leg. The heat from the warming device warms the blood and warms the hand. It will be appreciated that the extremity warming apparatus addresses the inadequacies of gloves and traditional use of handwarmers.

Figure 2:
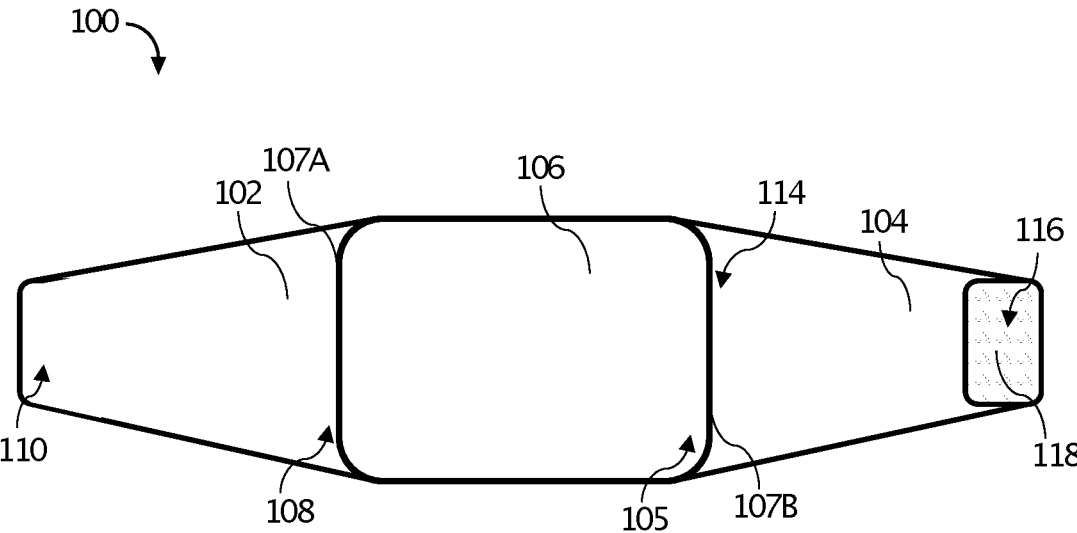
FIG. 2 illustrates a bottom plan view of a human extremity warming apparatus.

As shown in FIGS. 1-2, in one embodiment, a human extremity warming apparatus 100 (hereinafter referred to as "warming apparatus") comprises a first strap 102 and a second strap 104 with a compartment 106 interposed thereinbetween. In some embodiments, the compartment 106 may be integrated into the first and second straps 102, 104, creating a single unit. The compartment 106 may comprise an upper surface 103, a lower surface 105, a first side 107A, and a second side 107B. The first strap 102 may comprise a first end 108 and a second end 110. The first end 108 may be coupleable to the first side 107A of the compartment 106, and the second end 110 may comprise a first fastener 112. The second strap 104 may comprise a third end 114 and a fourth end 116. The third end 114 may be coupleable to the second side 107B of the compartment 106 on a side opposite the first end 108, and the fourth end 116 may comprise a second fastener 118.

In some embodiments, the first end 108 of the first strap 102 and third end 114 of the second strap 104 may be removably attachable to the compartment 106 via, for example, hook and loop, a hinge with a pin, or any other attachment mechanism. The first and second straps 102, 104 may comprise a material that may include, but is not limited to, nylon, polyester, silicone, leather, separately or some combination thereof.

Figure 4:
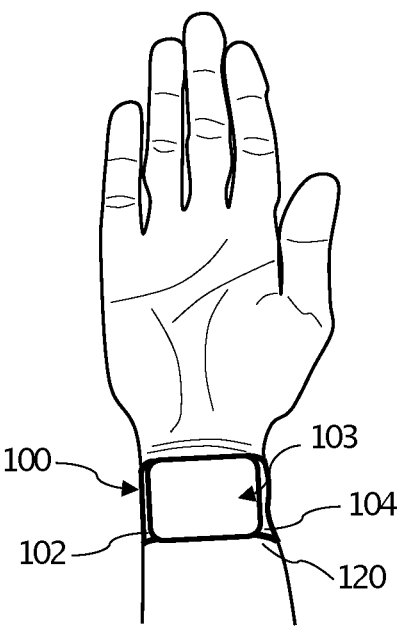
FIG. 4 illustrates top plan view of a human extremity warming apparatus coupled to a wrist of a user.

Furthermore, the first and second fasteners 112, 118 may couple to each other and be adjustable to fit wrists 120 of adults and children (as shown in FIG. 4). The first and second fasteners 112, 118 may comprise hook and loop so as to be attachable, adjustable, and detachable. Other first and second fasteners 112, 118 may include clasp fasteners, butterfly fasteners, buckles, hook and loop, magnets, or any other type of fastener.

Figures 3A, 3B:
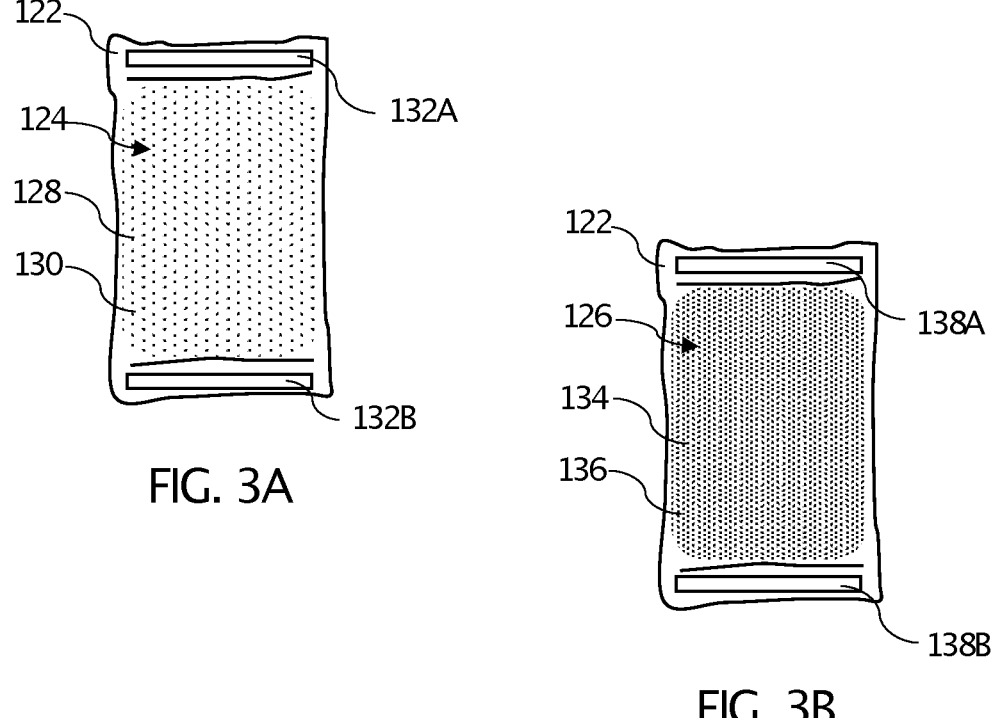
FIG. 3A illustrates a top plan view of a warming device of a human extremity warming apparatus.
FIG. 3B illustrates a bottom plan view of a warming device of a human extremity warming apparatus.

As shown in FIG. 3A-3B, the warming apparatus 100 comprises a warming device 122. The warming device 122 may include an air activated heating compound, a rechargeable battery warming device, or any other type of hand warming mechanism. The warming device 122 comprises an upper surface 124 and a lower surface 126. The upper surface 124 may comprise a first sheet of material 128. The first sheet of material 128 may comprise a heat transferring material 130 that provides the more heat to the user than the lower surface 124. However, due to the increased heat, that could potentially damage human skin, the upper surface 124 may be utilized when an undergarment is placed between the skin of the user and the warming device 122. In some embodiments, the upper surface 124 may be coupled to the compartment 106 via upper surface fasteners 132A, 132B, which may comprise hook and loop, magnets, or any other coupling mechanism. The compartment 106 may comprise hook and loop, or any other type of fastener, so as to receive the warming device 122. In other embodiments, the compartment 106 may comprise an adhesive that allows the warming device 122 to be releasably adhered thereto. When the upper surface 124 is coupled to the compartment 106 via the upper surface fasteners 132A, 132B, the lower surface 126 is exposed and capable of being placed on the wrist 120 of the user. The lower surface 126 may comprise a second sheet of material 134 that comprises a protective layer material 136 that transfers heat to the skin but prevents any burns upon the skin or overheating. In particular, the protective layer material 136 may release less heat than the heat transferring material 130. The lower surface 126 may be coupled to the compartment 106 via lower surface fasteners 138A, 138B, which may comprise hook and loop, magnets, or any other coupling mechanism. When the lower surface 126 is coupled to the compartment 106 via the lower surface fasteners 138A, 138B, the upper surface 124 is exposed.

In some embodiments, the upper surface 124 and lower surface 126 may be color coded to assist a user in determining the type of heating surface. For example, the upper surface 124 may be red so as to indicate a hotter surface that should not be placed directly against the skin and the lower surface 126 may be blue so as to indicate a heating surface that may be placed directly on the skin. While the upper and lower surfaces 124, 126 may be red and blue, respectively, it will be appreciated that the upper and lower surfaces 124, 126 may be any color or have any other indicia.

In some embodiments, as shown in FIG. 4, the warming apparatus 100 may be positioned on the underside of the wrist 120. Due to the placement of the warming device 122 on the underside of the wrist 120, the heat from the warming device 122 can warm the blood in the capillaries, veins, and arteries (e.g., radial and ulnar arteries), which makes for more efficient heat transfer to the hands and fingers. Accordingly, the hands of a user can remain warm while out in cold conditions. It will be appreciated that the warming apparatus 100 not only keeps hands warm but allows users to have free hands to perform any activity. While the warming apparatus 100 is shown on the wrist 120 of the user, it may be used on the chest, legs, upper arms, etc. Other uses for the warming apparatus 100 may be found for livestock, pets, or other animals. For example, in some embodiments, the length of the warming apparatus may increase for large animals. And, as shown in FIG. 1-2, the first and second fasteners 112, 118 may increase in length, width, and/or height to accommodate for larger animals.

Figure 5:
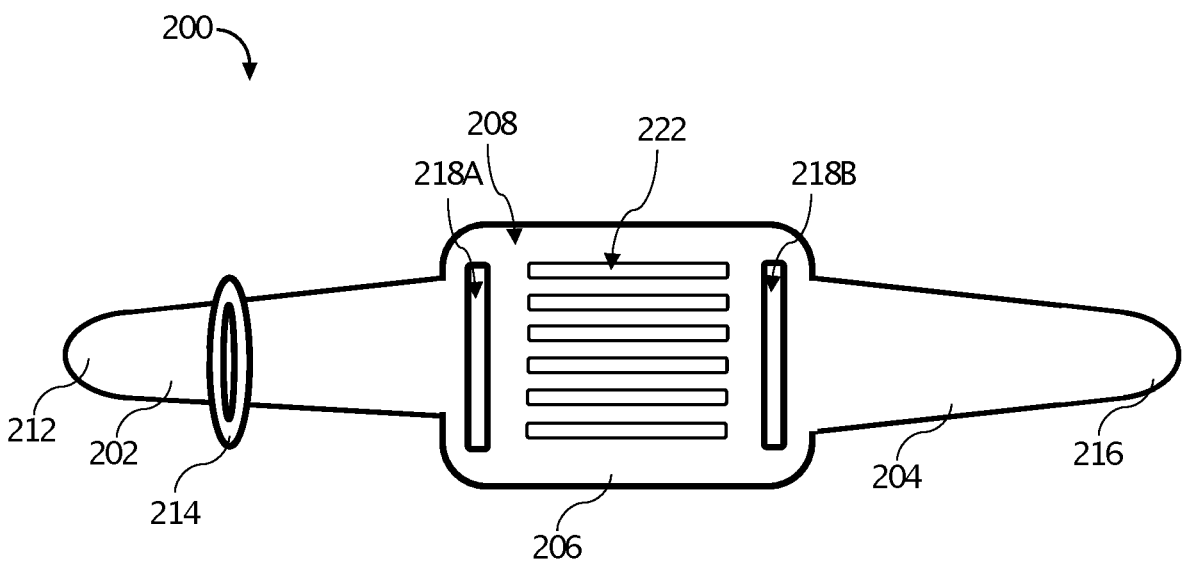
FIG. 5 illustrates a top plan view of a human extremity warming apparatus.
Figure 6:
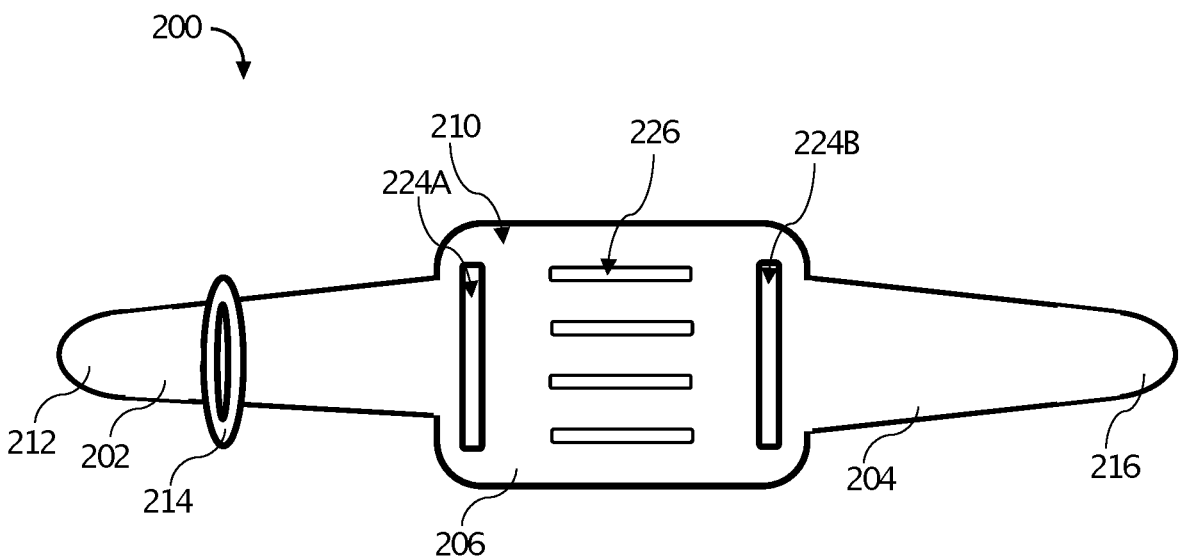
FIG. 6 illustrates a bottom plan view of a human extremity warming apparatus.
Figure 7:
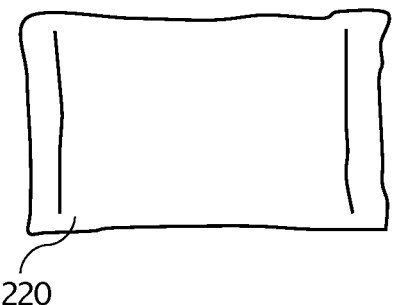
FIG. 7 illustrates a top plan view of a warming device.

As shown in FIGS. 5-7, in one embodiment, a human extremity warming apparatus 200 (hereinafter referred to as "warming apparatus") comprises a first strap 202 and a second strap 204 with a housing 206 interposed thereinbetween. The warming apparatus 200 may be manufactured from a silicon, nylon, or any other type of material. The housing 206 may comprise an upper surface 208 and a lower surface 210. The first strap 202 may comprise a first end 212. Approximate the first end 212, the first strap 202 may comprise a loop 214, which may be fixed or slidable on the first strap 202. The second strap 204 may comprise a second end 216 that can be inserted into the loop 214 so as to couple the second strap 204 to the first strap 202. While the loop 214 is shown, it will be appreciated that the first and second straps 202, 204 may couple to one another via, hook and loop, clasp fasteners, butterfly fasteners, buckles, side release buckles, hook and loop, magnets, or any other type of fastener. Furthermore, the first and second straps 202, 204 may couple to each other and be adjustable to fit wrists or ankles of adults and children.

The upper surface 208 of the housing 206 may comprise a first opening 218A and a second opening 218B capable of receiving a warming device 220. A user may insert the warming device 220 into either the first opening 218A or the second opening 218B. A user may also remove the warming device 220 from either the first opening 218A or the second opening 218B. The upper surface may have upper surface vents 222 to allow the heat to escape from the warming device 220 and contact the body of a user. While the vents 222 are shown as rectangular slits, it will be appreciated that the vents 222 may come in a variety of shapes and sizes, such as large circular apertures.

The lower surface 210 of the housing 206 may comprise a third opening 224A and a fourth opening 224B capable of receiving a warming device 220. A user may insert the warming device 220 into either the third opening 224A or fourth opening 224B. A user may also remove the warming device 220 from either the third opening 224A or fourth opening 224B. The lower surface 210 may have lower surface vents 226. The lower surface vents 226 may be less in number than the upper surface vents 222. As such, the lower surface 210 may release less heat than the upper surface 208. Accordingly, the lower surface 210 may be capable of contacting the skin of a user. In some embodiments, the lower surface 210 may not have any vents so as to transfer less heat to the skin of a user. While the vents 226 are shown as rectangular slits, it will be appreciated that the vents 226 may come in a variety of shapes and sizes, such as large circular apertures.

Figure 8:
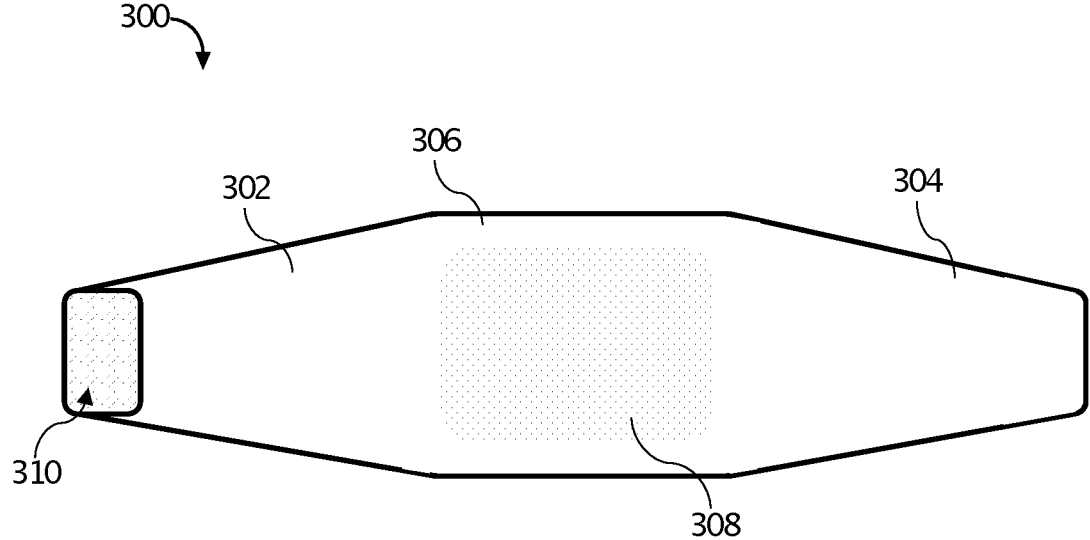
FIG. 8 illustrates a top plan view of a human extremity warming apparatus.

As shown in FIG. 8, in one embodiment, a warming apparatus 300 comprises a first strap 302 and a second strap 304 with a housing 306 interposed thereinbetween. The first strap 302, second strap 304, and housing 306 may be a single unit. In some embodiments, the warming apparatus 300 may be disposable. The housing 306 may comprise a warming device 308. In an alternate embodiment, the housing 306 may hold a warming device 308 against, for example, a wrist of the user, instead of being positioned within the housing 306. The warming device 308 may be similar to those described above, such as an air-activated warmer, battery, fuel, or any other type of warming device. The first strap 302 may couple to the second strap 304 via a first fastener 310 and a second fastener (Not shown). The first fastener 310 and second fastener may include hook and loop so as to be adjustable. Other first fasteners 310 and second fasteners may include snap buttons, buckles, magnets, or any other fastening mechanism.

In addition, the warming apparatus 100, 200, 300 may be utilized on a variety of locations on the human body and by numerous users, such as doctors and first responders. The warming apparatus 100, 200, 300, for example, may be used on the thigh, around the chest, or any other location so as to warm blood therein and ultimately, warm the core of the human body. In some embodiments, the warming apparatus 100, 200, 300 may utilize essential oils, copper fibers, or any other type of body aiding material. In some embodiments, the warming apparatus 100, 200, 300 may be used in conjunction with a smart watch or traditional watch.

Figure 9B:
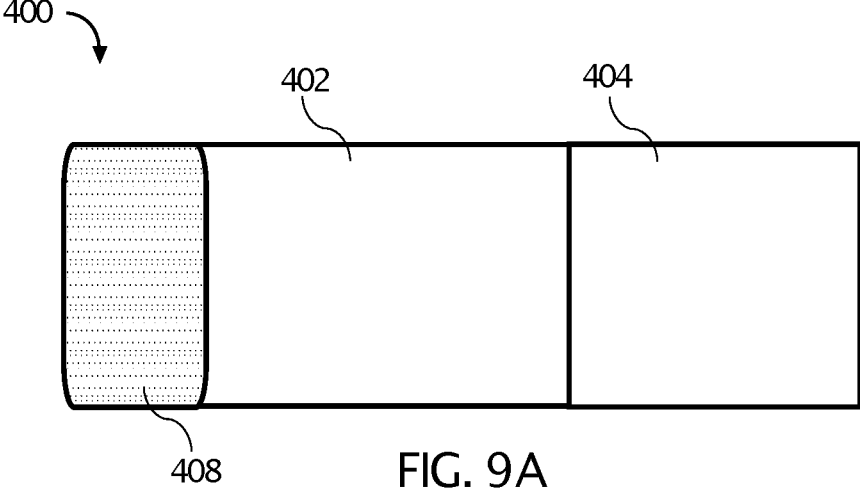
FIG. 9B illustrates a bottom plan view of a human extremity warming apparatus.
Figure 9B:
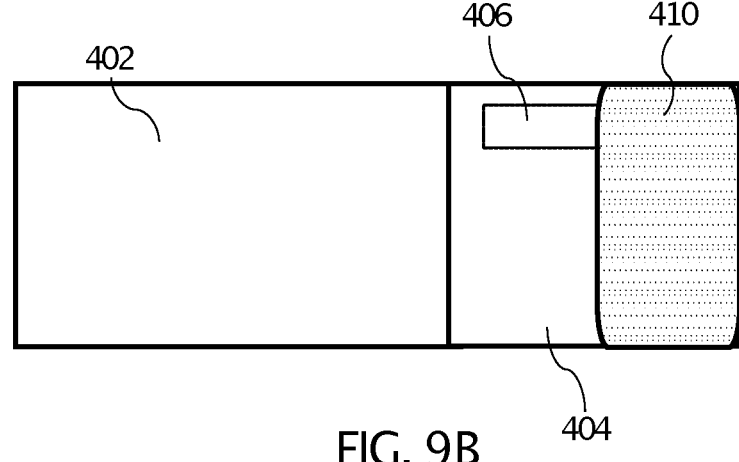

As shown in FIG. 9A-9B, a warming apparatus 400 comprises a first strap 402 with a housing 404. The warming apparatus 400 may be configured to wrap around the legs of livestock. While the housing 404 is shown at one end, it will be understood that the housing 404 may be interposed between the first strap 402 and a second strap. In some embodiments, the first strap 402, and housing 404 may be a single unit. In some embodiments, the warming apparatus 400 may be disposable. The warming apparatus 400 may be manufactured out of an impervious material, a non-impervious material, or some combination thereof. The housing 404 may receive a warming device that may be secured in the housing 404 via a housing fastener 406. In an alternate embodiment, the housing 404 may hold a warming device against, for example, a leg of a livestock or other types of animals. The warming device may be similar to those described above, such as an air-activated warmer, battery, fuel, or any other type of warming device. The first strap 402 may couple to the housing 404 via a first fastener 408 on the first strap 402 and a second fastener 410 on the housing 404. The first fastener 408 and second fastener 410 may include hook and loop so as to be adjustable. In some embodiments, the first fastener 408 may extend past an end of the first strap 402, thereby allowing the warming apparatus 400 to fit numerous sizes of livestock legs. Other first fasteners 408 and second fasteners 410 may include snap buttons, buckles, magnets, or any other fastening mechanism.

Figure 10:
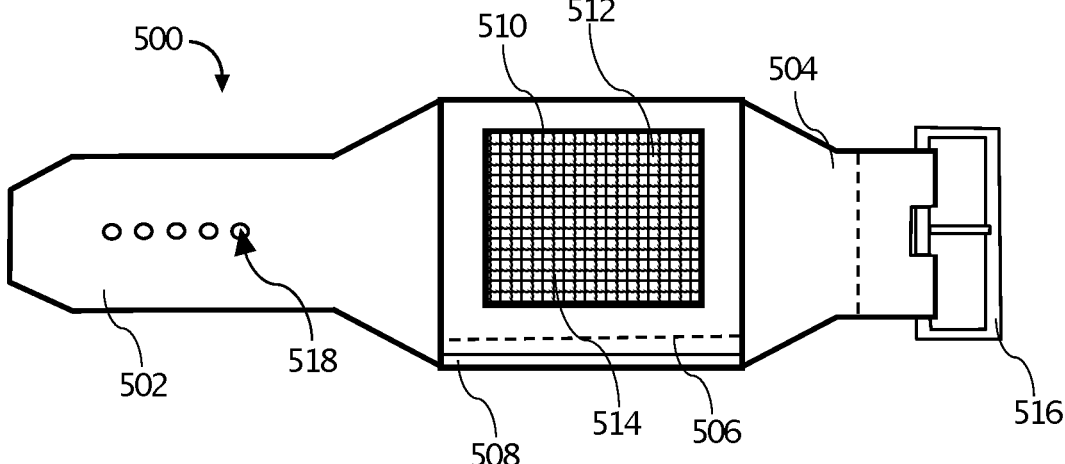
FIG. 10 illustrates a bottom plan view of a human extremity warming apparatus.

As shown in FIG. 10, a warming apparatus 500 comprises a first strap 502 and a second strap 504 with a housing 506 interposed thereinbetween. The housing 506 may be separate material from the first and second straps 502, 504. That is, the first and second straps 502, 504 may be manufactured from a different material than the housing and may be removably attachable to the housing 506. In some embodiments, the housing 506 and the first and second straps 502, 504 may be a single unit and manufactured from the same material. The apparatus 500 may comprise a first layer on a first side and a second layer on a second side. The first and second layers may be manufactured out of an insulative material and a heat-transferring material, respectively. The housing 506 may comprise a housing fastener 508 (e.g., hook and loop, snaps, magnets) that may be opened and closed so as to secure a warming device therein. In particular, when the fastener 508 is separated an opening is created, thereby allowing the warming device to be inserted into the housing 506. Then the housing 506 may be closed via the fastener 508. The warming device may be any of those previously discussed, air activated, battery, etc. The housing 506 may include a window 510. The window 510 may be covered by a screen 512 that is manufactured out of a first material 514. The first material 514 may include a mesh material or other heat-permeable material. It will be appreciated that the first material 514 allows heat from the warming device to pass to the user. While the screen 512 is shown in the window 510, it will be understood that in some embodiments, the window 510 may not include a screen, or may have a removably attachable screen. The window may be square-shaped (as shown), circular, or any other shape. The window 510 and screen 512 may be found on a single side of the housing 506 or on both sides of the housing 506. That is, a second window and a second screen may be positioned on a side of the housing opposite the window 510 and screen 512.

The warming apparatus 500 may be configured to wrap around the legs, arms, chest, of a human. In some embodiments, the warming apparatus 500 may also be used with animals. In some embodiments, the warming apparatus 500 may be disposable. The warming apparatus 500 may be manufactured out of an impervious material, a non-impervious material, or some combination thereof.

To attach the warming apparatus 500, the user may couple the first strap 502 to the second strap 504 via a first fastener 516 on the second strap 502. The first fastener 516 may include a clasp that is couplable to apertures 518 on the first strap 502. Other first fasteners 516 may include side release buckles, hook and loop, magnets, or any other coupling mechanism known in the art.

Figure 11A:
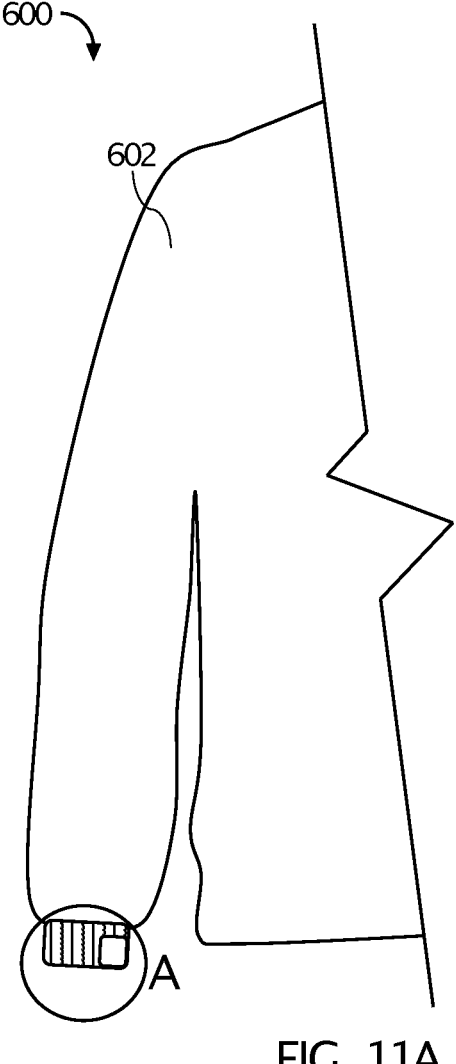
FIG. 11A illustrates a front elevation view of an article of clothing with a human extremity warming apparatus.
Figure 11B:
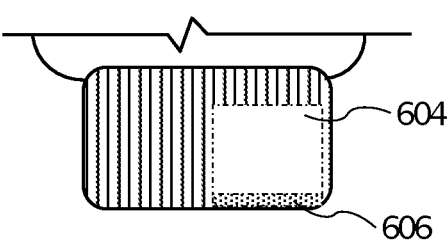
FIG. 11B illustrates a detailed view of a human extremity warming apparatus of circle A in FIG. 11A.

As shown in FIGS. 11A-11B, a warming apparatus 600 may be positioned in a sleeve, cuff, of an article of clothing 602 so as to be placed against a user's lower wrist. The warming apparatus 600 may comprise a housing 604 and a fastener 606 to provide access to the housing 604. The fastener 606 may include hook and loop, zipper, magnets, drawstrings, or any other type of fastening mechanism. The housing 604 may receive any of the previously mentioned warming devices.

Figure 12:
FIG. 12 illustrates a front elevation view of a clothing bottom with a human extremity warming apparatus.
Figure 12:
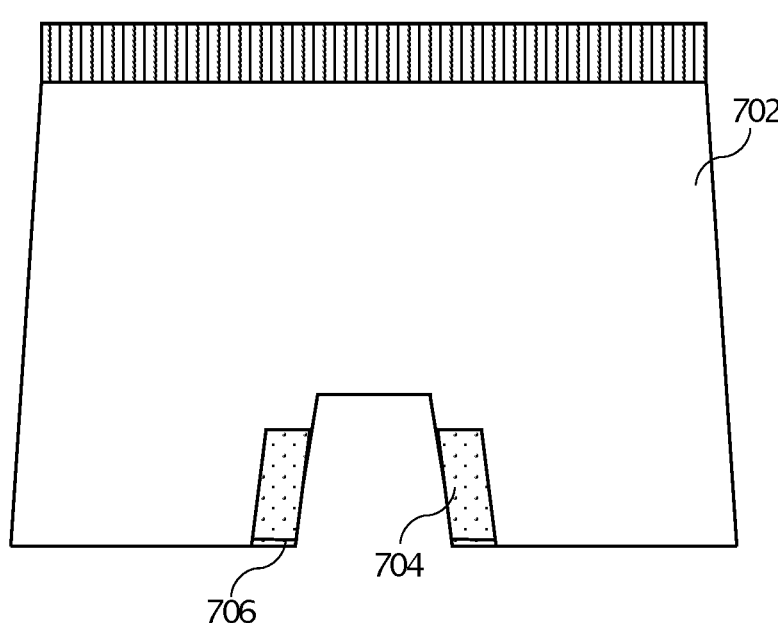

As shown in FIG. 12, a warming apparatus 700 may be placed on an inner leg portion of a bottom clothing article 702, such as boxers, briefs, and long underwear, thereby allowing the femoral artery to be warmed, and, thus, maintaining the warmth of the blood while passing to the feet. The warming apparatus 700 may comprise a housing 704 and a fastener 706. The housing 704 may receive a warming device. Once the warming device is inserted into the housing 704, the housing 704 may be sealed via the fastener 706.

Figure 13:
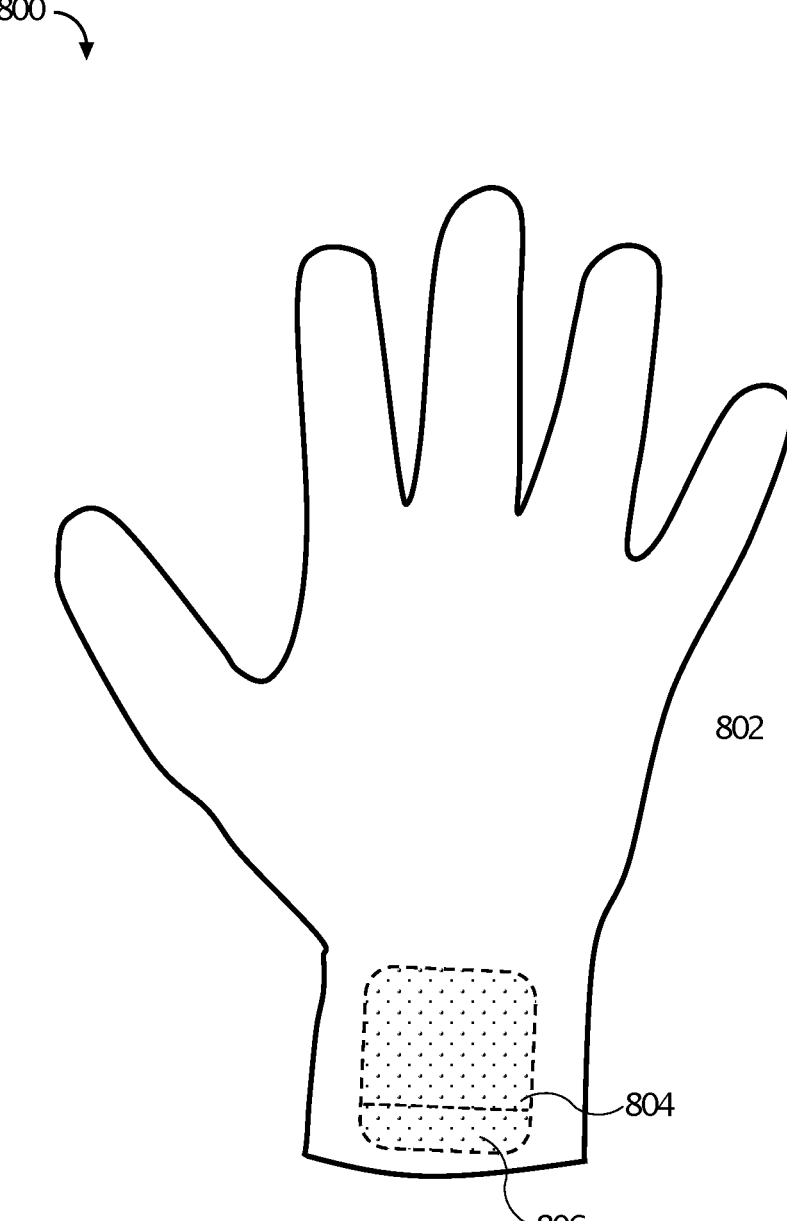
FIG. 13 illustrates a front elevation view of a glove with a human extremity warming apparatus.

Similarly, as shown in FIG. 13, a warming apparatus 800 may be integrated into a glove 802. The warming apparatus 800 may be positioned on a lower wrist portion of the glove 802, or any other position. The warming apparatus 800 may comprise a housing 804 to receive a warming device and a fastener 806 to secure the warming device therein. Access to the housing 804 may be found within the glove 802, or, in some embodiments, on an outer surface of the glove 802. The fastener 806 may comprise hook and loop, a zipper, magnets, or any other fastening mechanism. In some embodiments, the housing may include a heat-permeable layer of material, which may rest on a user's wrist, while an insulative layer of material may be placed on a side opposite the heat-permeable layer. The warming apparatus 600, 700, 800 may be manufactured from a mesh material, a non-vented material, or any other type of material to transfer heat to a user.

Figure 14A:
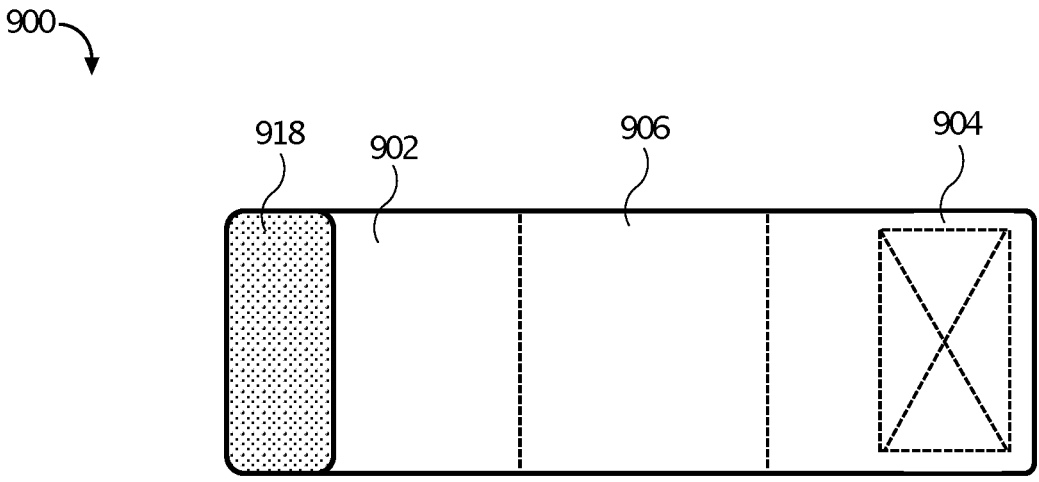
FIG. 14A illustrates a top plan view of a human extremity warming apparatus.
Figure 14B:
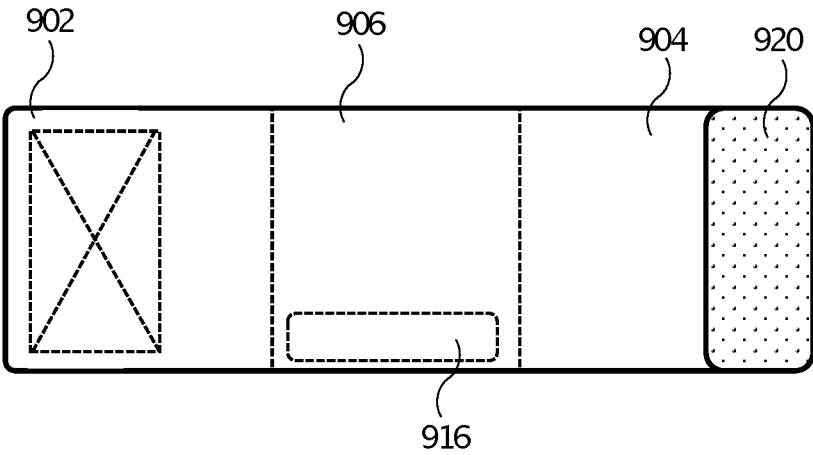
FIG. 14B illustrates a bottom plan view of a human extremity warming apparatus.
Figure 14C:
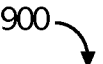
FIG. 14C illustrates a rear elevation view of a human extremity warming apparatus.
Figure 14C:
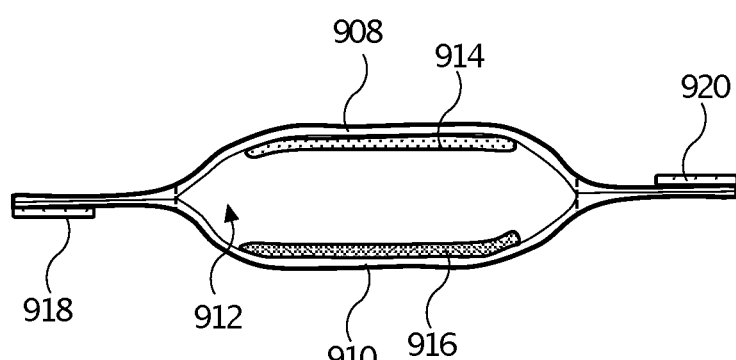

As shown in FIG. 14A-14C, a warming apparatus 900, which may include any characteristics of the previously mentioned embodiments, comprises a first strap 902 and a second strap 904 with a housing 906 interposed thereinbetween. The warming apparatus 900 may comprise a first layer of material 908 and a second layer of material 910. The first layer of material 908 may comprise a first material including flannel, fleece, or any other type of insulative material. The second layer of material 910 may also comprise a second material including polyester, nylon, of any other type of heat-transferring material. The first and second layers 908, 910 may be the same materials or different materials. In particular, in some embodiments, the first layer 908 may be a flannel material while the second layer 910 is a polyester material. Further, some material may act as a better conduit for heat transfer from a warming device positioned in the housing 906 to the user. As such, materials may be selected as a first and/or second layer 908, 910 depending on the amount of heat that is desired to be transferred. The warming apparatus 900 may be manufactured out of an impervious material, a non-impervious material, or some combination thereof.

The housing 906 may be created between the first layer 908 and the second layer 910. The housing 906 may be separate from the first and second straps 902, 904. The housing 906, when separated, may create an opening 912 to receive the warming device (similar to those discussed in previous embodiments). The housing 906 may comprise a first housing fastener 914 positioned on the first layer 908 in the opening 912 and a second housing fastener 916 positioned on the second layer 910 in the opening 912. When the housing 906 is secured, the first housing fastener 914 and the second housing fastener 916 are coupled together. The first and second housing fasteners 914, 916 may each comprise hook and loop, magnets, snaps, or any other fastening mechanism. The warming apparatus 900 may be configured to wrap around the legs, arms, chest, of a human. In some embodiments, the warming apparatus 900 may also be used with animals. In some embodiments, the warming apparatus 900 may be disposable.

To attach the warming apparatus 900, the first strap 902 may comprise a first fastener 918 and the second strap 904 may comprise a second fastener 920. The first fastener 918 may couple to the second fastener 920 and be adjusted to fit any user. The first and second fasteners 918, 920 may each comprise hook and loop. Other first and second fasteners 918, 920 may include side release buckles, magnets, clasps, or any other coupling mechanism known in the art.

Figure 15A:
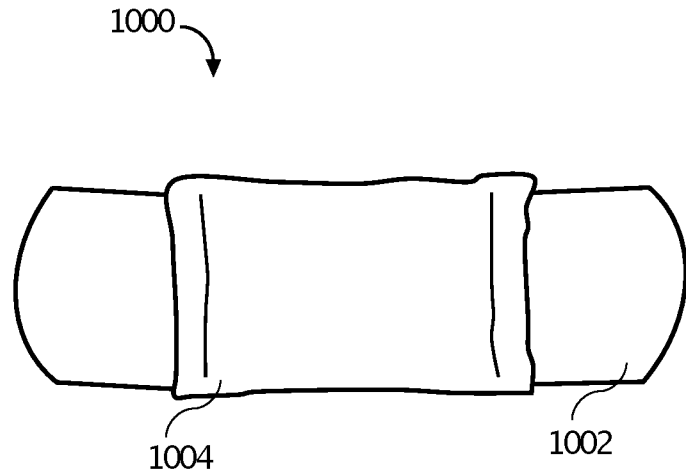
FIG. 15A illustrates a front elevation view of a human extremity warming apparatus.
Figure 15B:
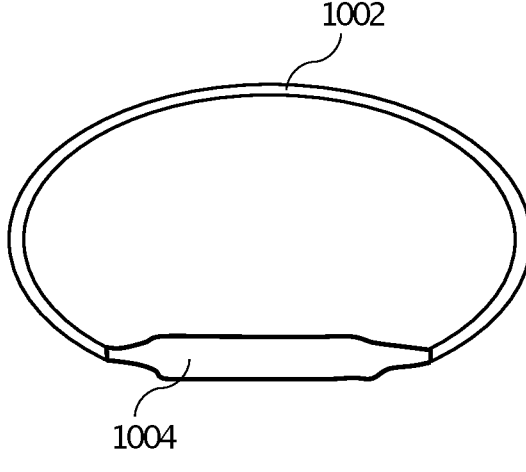
FIG. 15B illustrates a top plan view of a human extremity warming apparatus.

As shown in FIGS. 15A-15B, a warming apparatus 1000 may comprise a band 1002 and a warming device 1004 (similar to the other warming devices above). The band 1002 may comprise an extensible material, thereby allowing a user to stretch the band 1002 over an extremity to be secured thereon. The band 1002 may, in some embodiments, couple directly to the warming device 1004. The warming apparatus 1000 may be reusable or disposable depending on its configuration. In some embodiments, the warming apparatus 1000 may be reusable and comprise a housing to receive the warming device 1004. The housing may be made from a stretchable material so as to secure the warming device 1004.

It will be appreciated that any of the warming apparatuses found herein may include reflective insulative material. The warming apparatuses disclosed herein may prevent vasoconstriction for users and animals.

It will be understood that while various embodiments have been disclosed herein, other embodiments are contemplated. Further, systems and/or methods according to certain embodiments of the present disclosure may include, incorporate, or otherwise comprise properties or features described in other embodiments. Consequently, various features of certain embodiments can be compatible with, combined with, included in, and/or incorporated into other embodiments of the present disclosure. Therefore, disclosure of certain features or components relative to a specific embodiment of the present disclosure should not be construed as limiting the application or inclusion of said features or components to the specific embodiment unless stated. As such, other embodiments can also include said features, components, members, elements, parts, and/or portions without necessarily departing from the scope of the present disclosure.

The embodiments described herein are examples of the present disclosure. Accordingly, unless a feature or component is described as requiring another feature or component in combination therewith, any feature herein may be combined with any other feature of a same or different embodiment disclosed herein. Although only a few of the example embodiments have been described in detail herein, those skilled in the art will appreciate that modifications are possible without materially departing from the present disclosure described herein. Accordingly, all modifications may be included within the scope of this invention.

What is claimed is:

1. A human extremity warming apparatus comprising:
   a first strap comprising:
      a first end;
      a second end;
      a first fastener comprising hook and loop and extending from a first top edge to a first bottom edge;
   a second strap comprising;
      a third end;
      a fourth end;

a second fastener comprising hook and loop and extending from a second top edge to a second bottom edge;

a housing interposed between the first strap and the second strap, the first end of the first strap is coupled to a first side of the housing, and the third end of the second strap is coupled to a second side of the housing opposite the first side; wherein the housing extends from an upper edge to a lower edge of the human extremity warming apparatus, extending the entirety of the height of the human extremity warming apparatus;

a first layer and a second layer;

wherein the housing comprises a stretchable material and is positioned so as to rest upon the underside of the wrist of a user;

wherein the housing comprises an opening at the upper edge of the human extremity warming apparatus;

wherein the housing comprises a first housing fastener positioned proximate the opening and a second housing fastener proximate the opening, the first and second fasteners are removably attachable to each other:

wherein the first top edge, the second top edge, and the upper edge are on the same plane, and the first bottom edge, the second bottom edge, and the lower edge are on the same plane.

2. The human extremity warming apparatus of claim 1, further comprising a warming device that is secured in the housing, the warming device comprises an upper surface and a lower surface.

3. The human extremity warming apparatus of claim 2, wherein the upper surface comprises a first sheet of material, and the lower surface comprises a second sheet material.

4. The human extremity warming apparatus of claim 1, wherein the first layer comprises an insulative material on a first side of the apparatus.

5. The human extremity warming apparatus of claim 4, wherein the insulative material comprises flannel.

6. The human extremity warming apparatus of claim 1, wherein the second layer comprises a heat-transferring material on a second side of the apparatus.

7. The human extremity warming apparatus of claim 6, wherein the heat-transferring material comprises polyester.

8. The human extremity warming apparatus of claim 1, wherein the opening receives a warming device.

9. The human extremity warming apparatus of claim 1, wherein the first housing fastener and the second housing fastener comprise hook and loop.

10. A human extremity warming apparatus comprising:

a first layer comprising an insulative material;

a second layer comprising a heat-transferring material;

a first strap comprising;

a first end;

a second end;

a first fastener comprising hook and loop and extending from a first top edge to a first bottom edge;

a second strap comprising;

a third end;

a fourth end;

a second fastener comprising hook and loop and extending from a second top edge to a second bottom edge;

a housing comprising a stretchable material coupled to and interposed between the first strap and the second strap, the housing comprising an opening at an upper edge of the human extremity warming apparatus, the housing comprising a first housing fastener positioned on the first layer in the opening and a second housing fastener positioned on the second layer in the opening; wherein the housing extends from an upper edge to a lower edge of the human extremity warming apparatus, extending the entirety of the height of the human extremity warming apparatus;

a warming device comprising an upper heating surface and a lower heating surface, wherein the upper and lower heating surfaces are color coded to assist a user in determining the type of heating surface;

wherein the housing receives the warming device through the opening and is secured therein via the first housing fastener and the second housing fastener;

wherein the housing is positioned so as to rest upon the underside of the wrist of the user;

wherein the first and second housing fasteners comprise hook and loop:

wherein the first top edge, the second top edge, and the upper edge are on the same plane, and the first bottom edge, the second bottom edge, and the lower edge are on the same plane.

* * * * *